US005092972A

United States Patent [19]
Ghowsi

[11] Patent Number: 5,092,972
[45] Date of Patent: Mar. 3, 1992

[54] FIELD-EFFECT ELECTROOSMOSIS

[75] Inventor: Kiumars Ghowsi, Baton Rouge, La.

[73] Assignee: Board of Supervisors of Louisiana State University and Agricultural and Mechanical College, Baton Rouge, La.

[21] Appl. No.: 552,234

[22] Filed: Jul. 12, 1990

[51] Int. Cl.$^5$ ............................................. G01N 27/26
[52] U.S. Cl. ............................. 204/182.1; 204/180.1; 204/182.2; 204/299 R
[58] Field of Search ............ 204/299 R, 180.1, 182.2, 204/182.1

[56] References Cited

U.S. PATENT DOCUMENTS 4,931,328 6/1990 Swedberg ........................ 204/180.1

FOREIGN PATENT DOCUMENTS 137143 10/1981 Japan ............................... 204/299 R

OTHER PUBLICATIONS

Terry et al., "A Gas Chromatographic Air Analyzer Fabricated on a Silicon Wafer", IEEE Trans. Electron Devices, vol. ED-26, pp. 1880-1886 (1979).
Ewing et al., "Capillary Electrophoresis", Analytical Chemistry, vol. 61, No. 4, pp. 292A-303A (1989).
Jorgenson et al., "Zone Electrophoresis in Open-Tubular Class Capillaries", Anal. Chem., vol. 53, pp. 1298-1302 (1981).
Lauer et al., "Zone Electrophoresis in Open-Tubular Capillaries—Recent Advances", Trends in Analytical Chemistry, vol. 5, No. 1, pp. 11-15 (1986).
McCormick, "Capillary Zone Electrophoretic Separation of Peptides and Proteins Using Low pH Buffers in Modified Silica Capillaries", Anal. Chem., vol. 60, pp. 2322-2328 (1988).
Terabe et al., "Electrokinetic Separations with Micellar Solutions and Open-Tubular Capillaries", Anal. Chem., vol. 56, pp. 111-113 (1984).
Terabe et al., "Electrokinetic Chromatography with Micellar Solution and Open-Tubular Capillary", Anal. Chem., vol. 57, pp. 834-841 (1985).
Petersen, "Silicon as a Mechanical Material", Proceedings of the IEEE, vol. 70, No. 5, pp. 420-457 (1982).

Primary Examiner—John Niebling
Assistant Examiner—Arun S. Phasge
Attorney, Agent, or Firm—John H. Runnels

[57] ABSTRACT

Apparatus and process for controlling the rate of electroosmosis due to a first electric potential in an electrically insulating capillary, in which a second electric potential is applied between the electrically insulating walls of the capillary and a liquid within the capillary. This second electric potential changes the charge on the wall of the capillary, and thus allows manipulation of the zeta potential within the capillary, and therefore the rate of electroosmosis.

12 Claims, 7 Drawing Sheets

FIELD-EFFECT ELECTROOSMOSIS

BACKGROUND OF THE INVENTION

Charged species in solution or suspension in a liquid will migrate under the influence of an applied electric field in a phenomenon known as electrophoresis. Different species have different electrophoretic mobilities, providing a mechanism for separating different species. Coupling this separation means with a detecting means gives an analytical technique known as capillary zone electrophoresis.

Electroosmosis is the flow of liquid, generally a polar liquid, in contact with a porous solid, under the influence of an applied electric field. Electroosmosis has been attributed to the formation of an electric double layer at the solid/liquid interface. Under the influence of an electric field parallel to that interface, a portion of the liquid's diffuse layer moves, because of the electric forces acting on the excess ionic charge in that layer, and a shear plane is set up at some distance from the interface. A constant flow rate is reached when the force exerted on the ions (and thus on the liquid as a whole) is balanced by the frictional forces arising from the viscosity of the liquid. The electric potential at the shear plane is called the zeta potential, represented by z or the Greek letter "zeta."

The linear velocity, v, of the liquid under the influence of an applied electric field E is approximately $$, v=(e/h)E\ z \tag{1}$$

where e is the dielectric constant of the liquid, and h is the viscosity of the liquid.

Thus v is proportional (or approximately proportional) to the zeta potential, z. The magnitude of the zeta potential depends on, among other things, the particular liquid, the nature of the solid surface, and the concentrations of different species in the liquid. Polar solvents, such as water, can give rise to zeta potentials of as much 100 mV in contact with either polar or non-polar surfaces.

Electroosmosis can either augment or interfere with capillary electrophoresis. In can interfere because electroosmotic mobility is typically greater than are electrophoretic mobilities, limiting the time available for electrophoretic processes to separate different species before electroosmosis flushes the species out of the capillary.

One method to control the rate of electroosmosis is to change the voltage applied across the length of the capillary, but such a change also affects the rate of electrophoresis, and will not significantly affect the overall degree of electrophoretic separation. Other methods of controlling the rate of electroosmosis are to change the concentrations of species in solution or suspension, to change the pH, or to change the nature of the material forming the inner layer of the capillary. None of these methods is flexible or capable or rapid change, and each has other disadvantages as well.

There have been a number of recent efforts to make chemical sensors using microfabrication techniques. Most microsensors fabricated to data have used a two-step detection means. In the first step, chemical selectivity is accomplished by means of a chemical transformation, or by physisorption onto a chemically selective coating. In the second step, a physical consequence of the first step—e.g., a release of heat, a change in optical absorption, etc.—is converted to an electrical signal by means of a suitable microtransducer. Examples of chemical microsensors are the ISFET and the CHEMFET.

In conventional chemical sensors, the analyte is measured in the presence of other species. The selectivity component of the sensor ideally should respond only to the analyte. An alternative means of chemical analysis is first to separate the analyte from background species, and then to sense it with the detector. The detector in such a case need not be selective. An example of this type of chemical sensor is the micro-gas chromatograph developed by Terry et al., "A Gas Chromatographic Air Analyzer Fabricated on a Silicon Wafer," IEEE Trans. Electron Devices, Vol. ED-26, pp. 1880–86 (1979). Such chemical sensors may be called separation-based chemical microsensors. In addition to other factors favoring miniaturization, chromatographic systems also benefit from scaling laws—generally a decrease in column diameter results in an increased separation efficiency per unit length, or faster separations with short columns.

In capillary electrophoresis, a buffer-filled capillary is placed between two buffer reservoirs, and a potential field is applied across this capillary. The electric field creates an electroosmotic flow of buffer, generally toward the cathode. The electric field also causes electrophoretic flow of ionic solutes. The electrophoretic flow will generally be at a different rate from that of the electroosmotic flow. The difference between the electrophoretic mobilities of the solutes causes their separation. The separated species may be detected when they reach the cathode or anode, typically the cathode. Ewing et al., "Capillary Electrophoresis," Analytical Chemistry, Vol. 61, No. 4, pp. 292A–303A (1989).

A disadvantage of existing methods of capillary electrophoresis is the fact that the rate of electroosmotic flow is often high enough, compared to the electrophoretic mobilities, that electroosmotic flow carries the species out of the capillary before adequate separation of the species occurs. It is known that maximum resolution results when electroosmotic mobility just balances electrophoretic mobility. It has previously been though that such an approach required a lengthy analysis time. See Ewing et al., supra, at p. 298A; Jorgenson et al., "Zone Electrophoresis in Open-Tubular Glass Capillaries," Anal. Chem. Vol. 53, pp. 1298–1302 (1981). The desirability of thus tuning electroosmosis to achieve a high-resolution separation, and then re-tuning the electroosmotic flow to sweep separated components to a detector, has been recognized in the art. See Lauer et al., "Zone Electrophoresis in Open-Tubular Capillaries—Recent Advances," Trends in Analytical Chemistry, vol. 5, no. 1, pp. 11–15 (1986), at p. 13. Despite this recognition, to the knowledge of the inventor there has been nor previously reported means for controlling the rate of electroosmosis which is simultaneously flexible, capable of rapid response, and capable of changing the rate of electroosmosis independently of the rate of electrophoresis.

Because the rate of electroosmotic flow is proportional to the zeta potential, the rate of electroosmotic flow may be controlled or even stopped by adjusting the zeta potential, preferably without changing the electric potential across the length of the capillary. But existing method of controlling the zeta potential having significant disadvantages. These methods include changing the concentrations of species in solution or suspension, to change the pH, or to change the nature of the material forming the inner layer of the capillary. None of these methods is flexible or capable or rapid change, and each has other disadvantages as well. For example, a zero zeta potential may be desired to eliminate electroosmosis, so that only electrophoresis occurs. In a silica capillary, an approximately zero zeta potential may be achieved with a pH of 2-3; but such an acidic environment denatures many proteins. See Jorgenson et al., supra, at p. 1301; McCormick, "Capillary Zone Electrophoretic Separation of Peptides and Proteins Using Low pH Buffers in Modified Silica Capillaries," Anal. Chem., Vol. 60, pp. 2322-28 (1988).

It has been observed that adding micelles to the liquid can allow the separation of neutral species as well as charged ones: A micelle may incorporate a neutral species into its interior, while the charge on the micelle's surface causes the micelle-neutral species complex to act as a charged species in the electrophoresis, permitting separations. See Terabe et al., "Electrokinetic Separations with Micellar Solutions and Open-Tubular Capillaries, " Anal. Chem., vol. 56, pp. 111-13 (1984); and Terabe et al. "Electrokinetic Chromatography with Micellar Solution and Open-Tubular Capillary," Anal. Chem., vol. 57, pp. 834-41 (1985); both of which are incorporated by reference.

SUMMARY OF THE INVENTION

Field effect electroosmosis, a novel means of controlling the rate of electroosmosis due to a first electric potential, has been discovered in which a second electric potential is applied between the electrically insulating walls of a capillary and the liquid. The second electric potential changes the charge on the wall of the capillary, and thus allows manipulation of the zeta potential within the capillary. Manipulation of the zeta potential in this manner permits flexibly and rapidly controlling the rate of electroosmosis independently of the rate of electrophoresis.

The zeta potential becomes a function of, among other things, the voltage applied between the insulating capillary walls and the liquid, the pH of the electrolyte, and the concentrations of other ions in the electrolyte. By adjusting these factors, particularly the voltage between the capillary walls and the liquid, the zeta potential may be manipulated to a degree not previously possible. By controlling this applied voltage, the zeta potential may be made uniform throughout the capillary; or it may be made to be zero throughout the capillary; or it may be made to vary in a chosen manner across the length of the capillary. These manipulations of the zeta potential may cause electroosmosis to stop, or may be used otherwise to control the rate of electroosmosis.

If the rate of electroosmosis is adjusted to be equal and opposite to the rate of electrophoresis of a certain species, that species will become essentially immobile within the capillary, so that it becomes possible to improve resolution, and to separate species which have very close electrophoretic mobilities.

A device applying this field-effect electroosmosis phenomenon is called a MIEEKFED, a "Metal-Insulator-Electrolyte-Electrokinetic Field-Effect Device." A MIEEKFED in electrokinetic applications is analogous is some ways to a conventional MOSFET-type transistor in electronic applications. In a MIEEKFED, the electrolyte flow may be controlled, while in a MOSFET the electric current flow may be controlled—in either case, by means of an electric field applied perpendicular to the respective flow.

In a conventional MOSFET, an electric potential difference applied between the gate electrode and the substrate causes a change in the electric field orthogonal to the $SiO_2$—Si interface, resulting in modulation of the channel conductance. By replacing the silicon with an electrolyte which is free to flow, a MIEEKFED results. The voltage at the outer surface of the double layer controls the velocity of the electrolyte flow.

A MIEEKFED, which may be thought of as a field effect electrokinetic transistor, adds a new dimension to capillary electrophoresis separation-based sensors. A MIEEKFED can improve separations between different species whose mobilities would otherwise be very close using conventional techniques of capillary electrophoresis.

Applications of MIEEKFED's include capillary electrophoresis and other separation-based sensors. Capillary electrophoresis may be conducted with no electroosmotic flow by selecting the applied field to produce a zero zeta potential. This zero zeta potential may be flexibly achieved with or without altering the pH, the concentration of the electrolyte, or the inner layer of the capillary. A MIEEKFED is capable of rapidly and flexibly changing the zeta potential as a function of time.

Using a MIEEKFED in a capillary electrophoresis apparatus results in a number of advantages. The zeta potential, and therefore the rate of electroosmosis, may be flexibly controlled without unwanted restrictions on pH, electrolyte concentration, or the inner layer of the capillary. This degree, of flexible control allows improved electrophoretic separation of different species with close electrophoretic mobilities, which can otherwise be difficult to separate. Such a device built in accordance with the present invention can also be used to reduce the degree of "tailing" commonly observed in capillary electrophoresis of macromolecules. The tailing can be reduced by using a MIEEKFED to create a low, and preferably uniform, zeta potential.

The MIEEKFED has great potential for miniaturization, particularly in light of recent advances in the technology of micro-machining silicon. See Peterson, "Silicon as a Mechanical Material," Proceedings of the IEEE, Vol. 70, No. 5, pp. 420-457 (1982), which is incorporated by reference.

DETAILED DESCRIPTION OF THE INVENTION

A physical embodiment of the present invention has not been constructed to date—however, computer simulations have been most promising.

A MIEEKFED comprises an insulating capillary having an inner bore, and coated on the outside with a conducting layer; or alternatively, a conducting capillary coated on the inside with an insulating layer. Voltages are applied both across the length of the capillary, and "perpendicular" to the capillary—meaning that the voltage is applied between the liquid and the conducting layer. Although a capillary is preferred, the present invention should work in other shapes of insulators having bores through them.

Figure 1A:
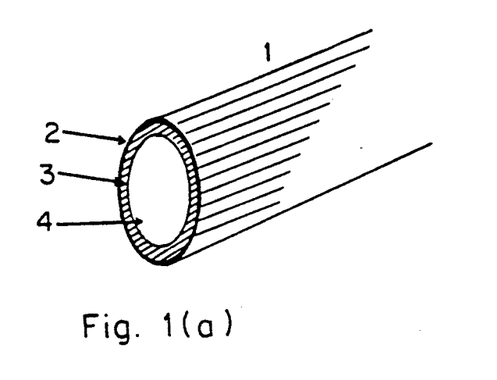
FIG. 1a and 1b illustrates a perspective view and a plan view of a MIEEKFED.
Figure 1B:
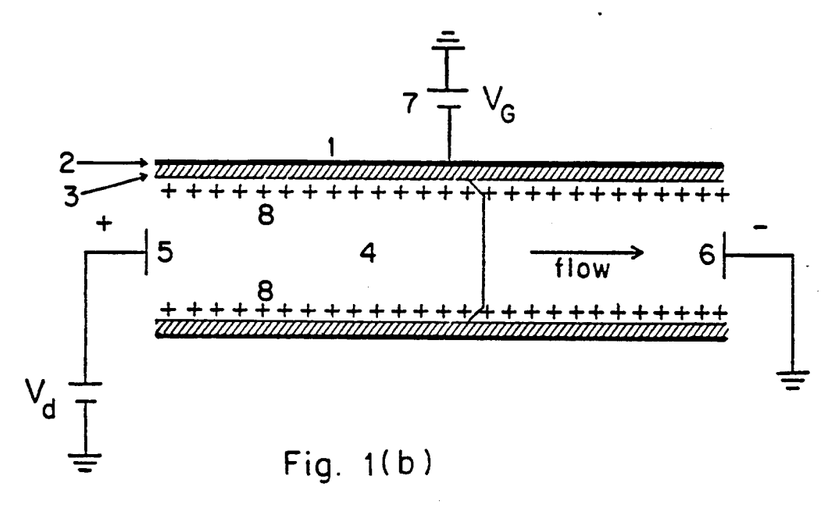

In a conventional MOSFET, an electric potential difference applied between the gate electrode and the substrate causes a change in the electric field orthogonal to the $SiO_2$—Si interface, resulting in modulation of the channel conductance. By replacing the silicon with and electrolyte which is free to flow, the MIEEKFED illustrated in FIG. 1 results. FIG. 1 illustrates a perspective view and a plan view of a MIEEKFED 1. A metal layer 2 surrounds and is in contact with insulator 3, which is a capillary having a bore through it. The bore of the capillary contains at least a part of electrolyte 4. Electrolyte 4 will typically comprise a polar liquid, such a water; may also comprise one or more ions; may also comprise one or more compounds in suspension or solution; and may also comprise one or more micelles. A first voltage $V_d$ is applied across the ends of the capillary between anode 5 and cathode 6. A second voltage $V_G$ is applied between electrode 7 and cathode 6. At the interface of insulator 3 and electrolyte 4, a double layer 8 is formed. The voltage at the outer surface of the double layer controls the velocity of electrolyte flow in the capillary.

A suitable material for the insulator is silica, or another insulating material with a high dielectric breakdown, preferably greater than 1 megavolt/cm, most preferably greater than 5 megavolt/cm, and is preferably silica, because of silica's high dielectric breakdown and existing micromachining techniques for silica.

Suitable materials for the conductor include materials of high conductivity which may readily be deposited on the insulator with a good electronic match, preferably aluminum or copper. The conducting layer not necessarily be a metal, although the expectation that it will usually be a metal is the reason for the initial "M" in the acronym MIEEKFED.

The thickness of the insulator is determined by the range of voltages which may practically be applied. Uniformity in thickness is desirable. There are competing considerations in determining the optimal thickness of the insulator layer. On the one hand, the thinner the layer, the smaller the voltage needed. On the other hand, it is difficult to fabricate very thin capillaries with uniform thickness, and such thin capillaries tend to be fragile. A compromise between these competing consideration must be reached. A preferred range for the insulator thickness in the case of silica will be 1-100 micron. The range 40-100 micron is pratical to fabricate by traditional means; below that range may be achieved by silicon micromachining techniques. The maximum perpendicular voltage that may be applied across the insulator is determined by the dielectric breakdown of the insulator. For silica, this breakdown occurs at a field of about 5-10 megavolt/cm.

Suitable methods for manufacturing the insulating capillary include redrawing, for thicknesses down to about 40 microns; thinner capillaries may be made through silicon micromachining techniques. See Petersen, supra, which is incorporated by reference. Suitable methods for manufacturing the conductive coating include chemical vapor diposition, and sputtering.

Figure 2:
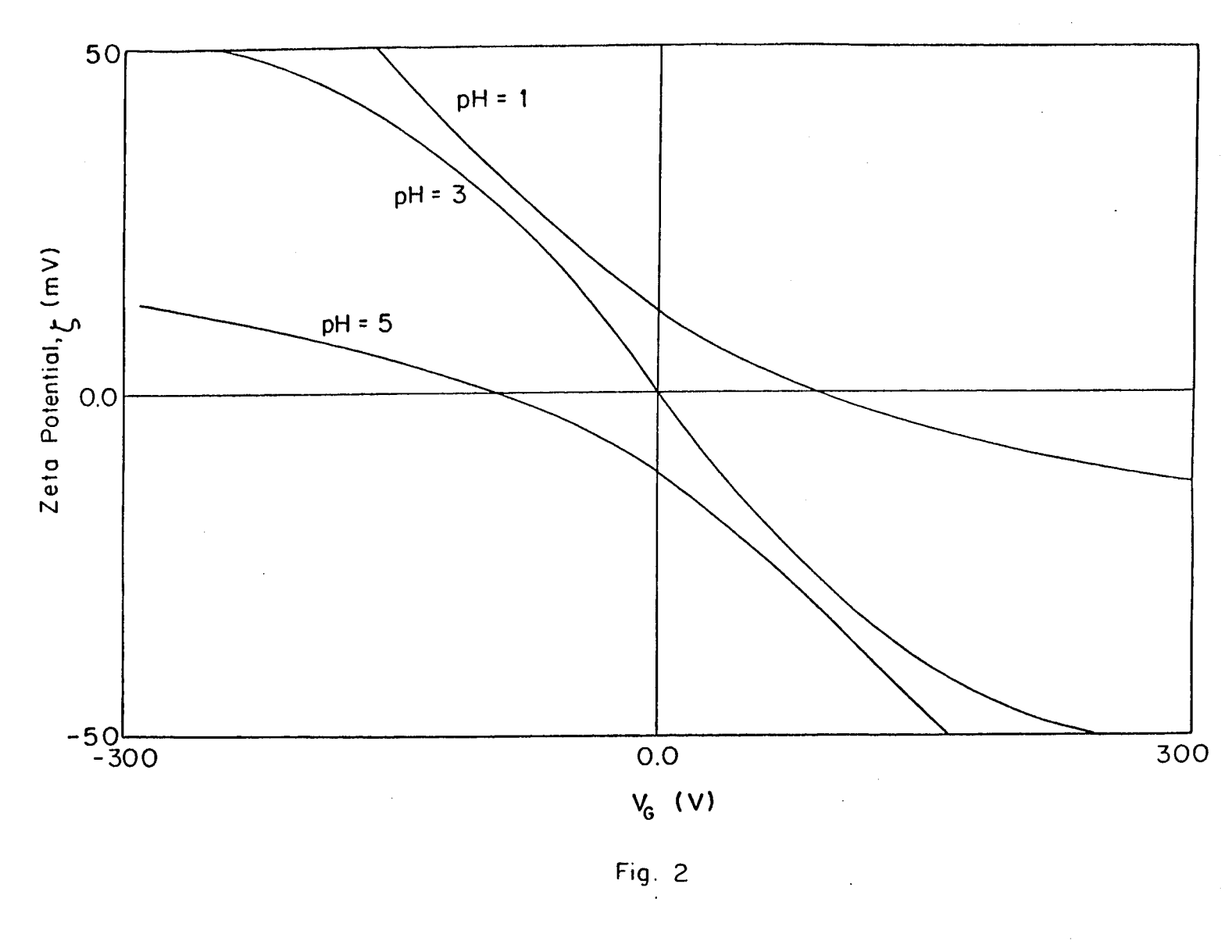
FIG. 2 illustrates computer calculations of the zeta potential in a MIEEKFED as a function of applied voltage, at different pH values, at a constant concentration of KCl.
Figure 3:
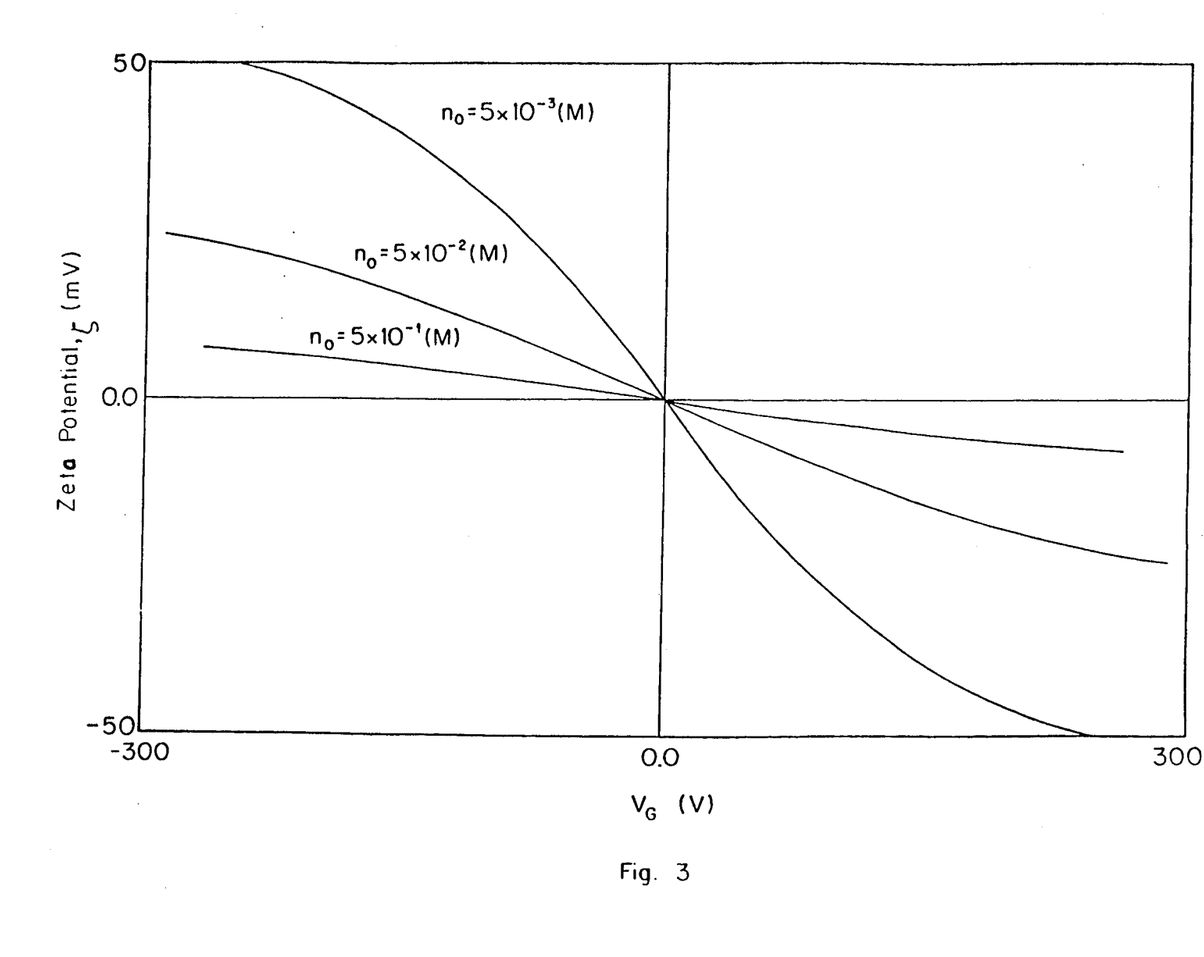
FIG. 3 illustrates computer calculations of the zeta potential in a MIEEKFED as a function of applied voltage, at different KCl concentrations and a constant pH.

FIGS. 2 and 3 illustrate computer calculations of the zeta potential as a function of $V_G$ for a 1-micron thick silica capillary, at different pH's, and at different concentrations $n_o$ of KCl in water, respectively. In these Figures, $V_G$ ranges from $-300$ to $+300$ volts, which corresponds to a maximum electric field of $3 \times 10^6$ V/cm, below the dielectric breakdown range for $SiO_2$ of about $5 \times 10^6$ to about $1 \times 10^7$ V/cm. In FIG. 2, the concentration of KCl in water is constant at 0.005 molar. In FIG. 3, the pH is constant at pH=3. Note that changing $V_G$ results in changing both the magnitude and the polarity of the zeta potential. Also note that when $V_G$ is close to zero, an incremental change in $V_G$ causes a greater change in the zeta potential than does the same incremental change when $V_G$ is larger. It is also apparent from FIG. 3 that a larger change in the zeta potential results from the same change in $V_G$ at lower ionic concentrations than at higher ionic concentrations.

The dependence of the zeta function on $V_G$ is complicated, and may either be observed empirically, or estimated through computer calculations as shown in FIGS. 2 and 3. This dependence may be written as $$V_G = f(z)$$
$$(V_d = 0)$$

or $$z = f^{-1}(V_G)$$
$$(V_d = 0)$$

In a MIEEKFED, a second voltage $V_d$ is applied across the length of a capillary of length L, so z is a function of distance x along the capillary as well:

$$z(x) = f^{-1}\left(V_G - \frac{x}{L} V_d\right) \tag{2}$$

Substituting equation (2) into equation (1), and substituting $V_{d/L}$ for E, gives the field-effect electroosmosis velocity:

$$v(x) = \left(\frac{e}{hL}\right) V_d f^{-1}\left(V_G - \frac{x}{L} V_d\right) \tag{3}$$

Equation (3) suggests that the velocity varies with distance; but because a liquid is essentially incompressible, the true velocity should be approximately equal to the average value of the above expression for v(x) over the range x=0 to x=L.

In a short capillary, a small potential will suffice to move the electrolyte, so it is feasible to have $V_d << V_G$. In this case, equation 3 may be approximated:

$$v \approx \left(\frac{e}{hL}\right) V_d f^{-1}(V_G) \quad (4)$$

Figure 4:
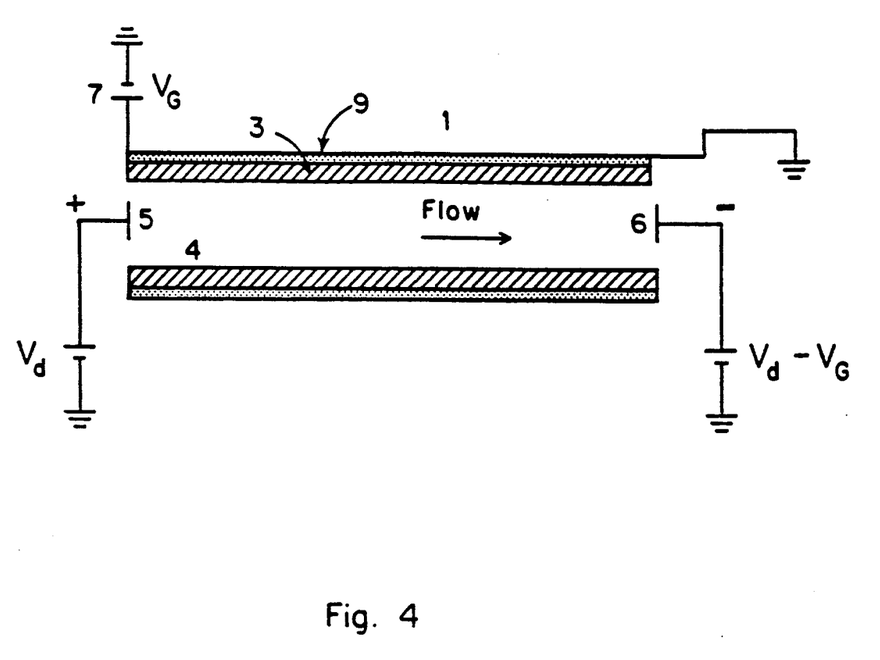
FIG. 4 illustrates MIEEKFED with an electric circuit capable of creating a constant zeta potential.

The zeta potential along the length of the capillary can be made constant through the use of a circuit such as that illustrated in FIG. 4. The zeta potential will be constant at $f^{-1}(V_G-V_d)$.

In FIG. 4, compared to FIG. 1, the position of electrode 7 is changed, and resistive layer 9 has replaced metal layer 2. A new voltage $V_G-V_d$ has also supplied to one end of the capillary bore. Suitable methods for making resistive layer 9 include growing a resistive layer on the insulator by sputtering or chemical vapor deposition, or by growing silica on silicon on a microchip, as for example, by the technique of Petersen, supra, which is incorporated by reference. Using an appropriate value of $V_G-V_d$, a constant zeta potential of any chosen magnitude may be chosen (within the limits imposed by the thickness and the dielectric breakdown of the insulator). In particular a zero zeta potential, and thus zero electroosmosis, may be achieved using the circuit of FIG. 4 and selecting appropriate $V_G$ and $V_d$. This result can be achieved without narrow limits on concentrations, pH's, or particular insulator materials, as has previously been the case.

More generally, an electroosmotic velocity v may be obtained, using the circuit of FIG. 4, from equation (3) by selecting $$V_G - V_d = f\left(\frac{vhL}{eV_d}\right)$$

Thus, for example, it might be desirable to separate and detect three species, A, B, and C of very close rates of electrophoresis, $v_A$, $v_B$, and $v_C$, respectively, where $v_A < v_B < v_C$. This result may be achieved using the capillary electrophoresis apparatus of FIG. 5. This apparatus incorporates the MIEEKFED 1 of FIG. 4, a buffer reservoir 10 feeding MIEEKFED 1, and a detector 11 for detecting components injected into MIEEKFED 1 as they exit the capillary.

Figure 5A:
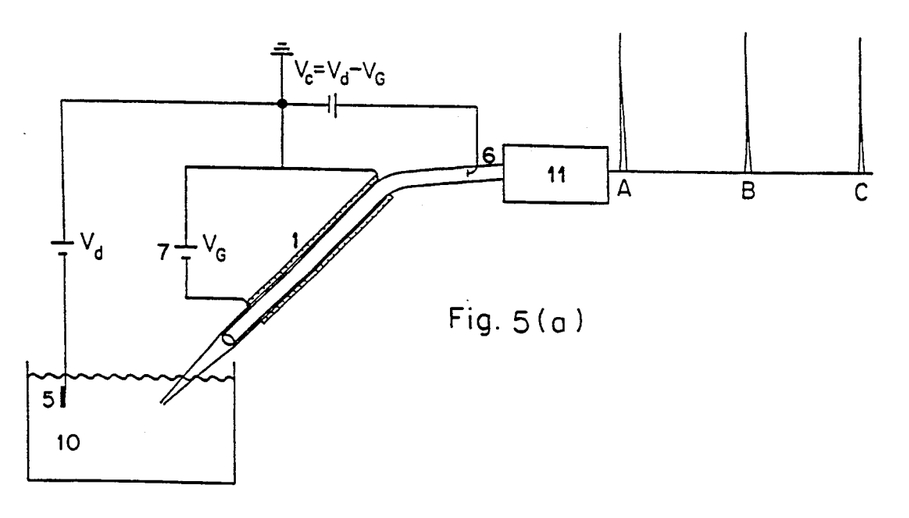
FIG. 5a and 5b illustrates a capillary electrophoresis apparatus incorporating a MIEEKFED.
Figure 5B:
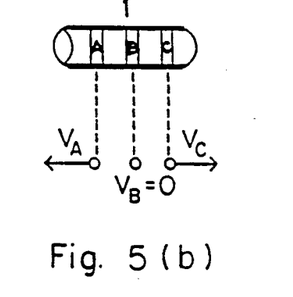

Selecting $V_G-V_d$ to give an electroosmosis rate equal to $-v_B$, species B will be essentially immobile in the capillary, while species A will move slowly towards the anode 5, and species C will move slowly toward the cathode 6, and be detected by detector 11. "Tuning" the voltages applied as a function of time can subsequently cause species B, and finally species A, to reach detector 11. Using conventional means of capillary electrophoresis chromatography, it can be difficult to separate species with very close electrophoresis mobilities. The MIEEKFED allows flexibly "tuning" the rate of electroosmosis to counterbalance electrophoresis, and to achieve better separations than would otherwise be possible in capillary electrophoresis, over a broader range of concentrations, pH's, insulator materials, etc.

Another application of the present invention is to reduce the degree of "tailing" commonly seen in capillary electrophoresis of macromolecules. Tailing is reduced by reducing the zeta potential in the capillary. Thus tailing can be controlled by using a MIEEKFED to create a very low, and preferably uniform, zeta potential.

Higher resolution, but slower speed, results from a lower zeta potential. On the other hand, a higher zeta potential results in lower resolution, but faster response times. The more dilute the concentration, the greater is the degree of control over the zeta potential. See FIG. 3.

Microfabrication techniques such as those of Petersen, above, are well suited for making MIEEKFED's, because of the need for thin layers in a MIEEKFED. One possibility is that of performing multiple capillary electrophoresis on a single chip, having several capillaries "tuned" to different species, and acting simultaneously in parallel.

Separations of neutral species in a MIEEKFED may be performed with micelles, as described in the two Terabe references cited supra, both of which are incorporated by reference. A neutral species is considered to be "associated" with a micelle if it shows an affinity for the micelle, even though it may associate, dissociate, and reassociate from time to time. Different micelles may be used to separate different neutral species, or the same micelle—provided that the different neutral species have different affinities for that micelle.

I claim:
1. An apparatus for controlling the electroosmotic flow of a liquid, comprising:
    (a) an electrical insulator having a capillary bore therein, the capillary bore having first and second ends and being capable of accommodating at least a portion of the liquid, wherein said insulator has a dielectric breakdown greater than about 1 megavolt per centimeter;
    (b) means for applying a first voltage between the first end of the capillary bore and the second end of the capillary bore; and
    (c) means, comprising an electrical conductor contacting said insulator, for applying a second voltage between a point within the insulator and point within the capillary bore;
wherein said apparatus is on a microchip.

2. An apparatus for controlling the electroosmotic flow of a liquid, comprising:
    (a) an electrical insulator having a capillary bore therein, the capillary bore having first and second ends and being capable of accommodating at least a portion of the liquid, wherein said insulator has a dielectric breakdown greater than about 1 megavolt per centimeter;
    (b) means for applying a first voltage between the first end of the capillary bore and the second end of the capillary bore;
    (c) means for applying a second voltage between a point within the insulator and a point within the capillary bore; and
    (d) means, in the vicinity of at least one of the ends of the capillary bore, for detecting components of the liquid; wherein said apparatus is on a microchip.

3. An article comprising a plurality of apparatuses as recited in claim 2, wherein at least two of said apparatuses are on the same microchip.

4. An apparatus comprising:
    (a) an electrically insulating capillary having a first end and a second end, said capillary having a bore therein, the bore having a first end and a second end;
    (b) means for applying a first voltage between the first end of the bore and the second end of said capillary;

(c) means for applying a second voltage between said first end of said capillary and said second end of said capillary;

(d) means for applying a third voltage between the second end of the bore and said second end of said capillary, wherein said third voltage is substantially equal to the difference between said second voltage and said first voltage.

5. An apparatus as recited in claim 4, wherein said second voltage means comprises an electrically resistive material contacting said capillary.

6. An apparatus as recited in claim 4, wherein said apparatus is on a microchip.

7. A process for controlling the electroosmotic flow of a liquid within an electrical insulator, comprising the steps of:

(a) applying a first voltage betweeen two points within the liquid; and (b) applying a second voltage between a point within the insulator and a point within the liquid;

wherein the liquid comprises a first charged component, and wherein said voltages are selected to produce an electroosmotic rate of flow of the liquid which is equal in magnitude, but opposite in direction, to the rate of electrophoresis of the first charged component, whereby the first charged component becomes essentially immobile relative to the insulator.

8. A process as recited in claim 7, wherein the liquid comprises a second charged component with an electrophoretic mobility different from the electrophoretic mobility of the first charged component, whereby the first and second charged components are separated from one another.

9. A process as recited in claim 8, wherein the first charged component comprises a micelle and a first uncharged component associated with the micelle; and wherein the second charged component comprises a micelle and a second uncharged component associated with the micelle; whereby the first charged component is separated from the second charged component; whereby the first uncharged component is separated from the second uncharged component.

10. A process as recited in claim 8, wherein the voltages are selected to generate a zeta potential sufficiently low to reduce significantly any tailing of at least one of the charged components.

11. A process as recited in claim 8, wherein at least one of the voltages changes as a function of time, whereby the mobilities of the charged components change as a function of time.

12. A process as recited in claim 8, additionally comprising the step of detecting at least one component of liquid.

* * * * *